US008815244B2

(12) United States Patent
Tsukamoto

(10) Patent No.: US 8,815,244 B2
(45) Date of Patent: Aug. 26, 2014

(54) METHOD FOR PRODUCTION OF ANTIBODY USING OSTRICH

(75) Inventor: Yasuhiro Tsukamoto, Osaka (JP)

(73) Assignees: Japan Science and Technology Agency, Saitama (JP); Osaka Prefecture University Public Corporation, Osaka (JP)

( * ) Notice: Subject to any disclaimer, the term of this patent is extended or adjusted under 35 U.S.C. 154(b) by 66 days.

(21) Appl. No.: 13/210,512

(22) Filed: Aug. 16, 2011

(65) Prior Publication Data
US 2011/0301336 A1  Dec. 8, 2011

Related U.S. Application Data

(62) Division of application No. 12/065,072, filed as application No. PCT/JP2006/316960 on Aug. 29, 2006, now abandoned.

(30) Foreign Application Priority Data

Aug. 29, 2005  (JP) ................................ 2005-246993

(51) Int. Cl.
*A61K 39/395* (2006.01)
*C07K 16/00* (2006.01)
*C07K 16/18* (2006.01)
*C07K 16/28* (2006.01)
*C07K 16/10* (2006.01)
*A61K 39/00* (2006.01)

(52) U.S. Cl.
CPC ................ *C07K 16/00* (2013.01); *C07K 16/18* (2013.01); *A61K 2039/505* (2013.01); *C07K 16/2803* (2013.01); *C07K 16/10* (2013.01); *C07K 16/2851* (2013.01); *C07K 2317/76* (2013.01); *C07K 2317/23* (2013.01)
USPC .................................... 424/153.1; 424/130.1

(58) Field of Classification Search
CPC . A61K 2039/505; A61K 39/00; A61K 38/00; C07K 16/18; C07K 16/02
See application file for complete search history.

(56) References Cited

U.S. PATENT DOCUMENTS

| | | | |
|---|---|---|---|
| 4,931,385 A | 6/1990 | Block et al. | |
| 5,367,054 A | 11/1994 | Lee | |
| 5,725,858 A | 3/1998 | Fioretti et al. | |
| 5,747,659 A | 5/1998 | Fioretti et al. | |
| 7,442,378 B2 | 10/2008 | Browning | |
| 2004/0241310 A1 | 12/2004 | Gizurarson | |
| 2005/0090001 A1 | 4/2005 | Parker | |
| 2005/0201911 A1 | 9/2005 | Namiki et al. | |
| 2006/0018897 A1 | 1/2006 | Lee et al. | |
| 2006/0293263 A1* | 12/2006 | Koide et al. | ..................... 514/44 |

FOREIGN PATENT DOCUMENTS

| | | |
|---|---|---|
| JP | 02-306924 A | 12/1990 |
| JP | 04-134097 A | 5/1992 |
| JP | 09-510702 A | 10/1997 |
| JP | 2001-238676 A | 9/2001 |
| JP | 2005-127754 | 5/2005 |
| KR | 2003-0079382 | 10/2003 |
| WO | 95/22980 A1 | 8/1995 |
| WO | 03/054021 | 7/2003 |
| WO | 2004/073393 | 9/2004 |
| WO | WO2004100966 | * 11/2004 ......... A61K 31/7052 |
| WO | 2005/044249 | 5/2005 |
| WO | 2005/056777 | 6/2005 |

OTHER PUBLICATIONS

Moving et al. (Adv Exp Med Biol, 1998; 440:495-9, Abstract only).*
Campbell (Monoclonal Antibody Technology, 1984, Chapter 1, pp. 1-32).
Office Action dated Feb. 7, 2013, issuing in U.S. Appl. No. 13/210,516.
Office Action dated May 17, 2013, issuing in U.S. Appl. No. 13/210,516.
Sakai, K., et al. Serological and Virological Studies of Newcastle Disease and Avian Influenza in Slaughter-Age Ostriches (*Struthio camelus*) in Japan. J. Vet. Med. Sci. 68(5): 491-494 (2006).
Office Action dated Aug. 26, 2010, issuing in Australian appln. No. 2006285850, pp. 1-2.
P. de Girolamo et al., "Presence of S100-like Protein in Non-mammalian Vertebrate Kidney," Veterinary Research Communications, vol. 27, Suppl. 1 (2003), pp. 591-593.
Office Action dated Jul. 15, 2009, issuing in Japanese appln. No. 2007-533254.
Blignaut A et al: Antibody responses to La Sota strain vaccines of Newcastle disease virus in ostriches (*Struthio camelus*) as detected by the enzyme-linked immunosorbent assay, Avian Diseases, vol. 44, No. 2, Apr. 2000, pp. 390-398.
Shivaprasad H L et al: Turlock-like bunyavirus associated with encephalomyelitis and myocarditis in an ostrich Chick. Journal of Veterinary Diagnostic Investigation. 14:363-370 (2002).
M. Spinu et al: "Haematological and immunological variables in a domesticated and wild subspecies of ostrich", British Poult Science 1999 40: 613-618.
Ricardo Luiz Moro de Sousa, et al: "Detection and Quantification of Antibodies to Newcastle Disease Virus in Ostrich and Rhea Sera Using a Liquid Phase Blocking Enzyme-Linked Immunosorbent Assay", Clinical and Diagnostic Laboratory Immunology, Nov. 2000. vol. 7, No. 6, pp. 940-944.
Genki Sakabe, et al: Preparation of Newcastle Disease (ND) Vaccine Program in Ostriches, 2003, pp. 163-164.

(Continued)

*Primary Examiner* — Sharon Wen
(74) *Attorney, Agent, or Firm* — Roylance, Abrams, Berdo & Goodman, L.L.P.

(57) ABSTRACT

Disclosed is an antibody produced using an ostrich. Also disclosed is a method for producing the antibody. By using an ostrich, it becomes possible to produce antibodies (particularly antibodies for medical use), which have been hardly produced by using the mammals such as the mouse and the rat, homogeneously in a single body, in large quantities and in a simple manner. The method can overcome a disadvantage of lot-to-lot variation which may occur in the production of polyclonal antibodies using other animals.

2 Claims, 6 Drawing Sheets

(56) References Cited

OTHER PUBLICATIONS

Chang, Mau-Sun et al: "Antibody detection of SARS-CoV spike and nucleocapsid protein", Biochemical and Biophysical Research Communications 314 (2004), pp. 931-936.
Boli Zuo, et al: "Piezoelectric Immunosensor for SARS-Associated Coronavirus in Sputum", Anal. Chem, 2004. 76:3536-3540.
R&D Systems, Inc., Product Data Sheet for Anti-human MCAM/CD146 Antibody, Catalog No. AF932, May 14, 2008.
R&D Systems, Inc., Product Data Sheet for Monoclonal Anti-human MCAM (CD146) Antibody, Catalog No. MAB932, Dec. 12, 3003.
R&D Systems, Inc., Product Data Sheet for Anti-human ALCAM Antibody, Catalog No. AF656, Mar. 22, 2005.
R&D Systems, Inc., Product Data Sheet for Monoclonal Anti-human ALCAM Antibody, Catalog No. MAB6561, Aug. 1, 2003.
Extended European Search Report, dated Mar. 10, 2009, for EP appln. No. 06796940.2.

* cited by examiner (a)

(b)

METHOD FOR PRODUCTION OF ANTIBODY USING OSTRICH

The present application is a divisional of U.S. application Ser. No. 12/065,072, filed Feb. 27, 2008, which is the U.S. National phase entry under 35 U.S.C. §371 of International Application PCT Patent Application No. PCT/JP2006/316960, filed on Aug. 29, 2006, which claims priority to Japanese Patent Application No. 2005-246993, filed on Aug. 29, 2005. The International Application was published under PCT Article 21(2) in a language other than English. The contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

Background Art

Conventional animals used for production of antibodies are, for example, the mouse, the rat, the sheep and the goat. These mammals, however, have their proteins which are highly similar to the human proteins and therefore, it is often difficult to produce an antibody that suppresses function of a specific human protein by using these animals. In other words, even if these animals are immunized against a human molecule (for example, a human protein) that relates to a certain disease, it was often difficult to produce a desired antibody (particularly, an antibody for treatment) within these animals.

On the other hand, the production of anti-human antibodies for treatment or diagnosis by using the chicken, which is far apart from the human, has been recently attempted (for example, Japanese Laid-Open Patent Publication No. 2001-238676). However, this method has the problem that it is difficult to produce a large amount of homogeneous antibodies, because the chicken has very little blood. Moreover, a conventional method for producing a monoclonal antibody has the problem that many cell cultures, media for the cell cultures and complicated work are needed in order to produce a sufficient amount of antibodies.

DISCLOSURE OF INVENTION

The preset invention is made to solve the above-mentioned problems and intended to provide a novel method for producing a large amount of homogeneous antibodies in a simple manner (particularly, a method for producing antibodies which were difficult to produce by conventional methods using the mammals).

In order to solve the above-mentioned problems, the present inventor focused on use of the ostrich of a large-size bird. As a result of research and analysis, the present inventor has found the following points, which led to the present invention;
(1) By immunizing the ostrich, it becomes possible to easily produce an antibody detecting an antigen protein (or part thereof) highly reserved among the mammals, which was difficult to produce by conventional methods using the mouse and the rabbit.
(2) Using the antibody produced by using the ostrich, western blot analysis and immunocytochemistry were carried out. As a result, the antibody was able to specifically detect the target protein (CD166 protein) which is a cancer marker and thus, the antibody can be used as an antibody for diagnosis.
(3) The above anti-CD166 antibody, produced by using the ostrich, also had antitumor effect of suppressing tumor growth. Therefore, the antibody can be also used as an antibody for treatment.

That is, the present invention provides an antibody produced by using the ostrich and method for production thereof. The ostrich is now becoming a farm animal (used for food) and the number of ostrich farms is also increasing in Japan. Food for keeping the ostrich can be purchased on the market, and its nutrition efficiency is very high. The ostrich can reach about as much as 120 kg in weight and it is possible to collect a large amount of blood from a single ostrich, which corresponds to an amount of almost 100 chickens' blood. That is, it becomes possible to produce a large amount of homogeneous antibodies for treatment (or diagnosis) by using a single ostrich, which were difficult to produce by using the mammals such as the mouse and the rat. Thus, the present invention can overcome the problem of lot-to-lot variation when producing polyclonal antibodies by using other animals. In addition, by using an infant ostrich, the immunization can be realized by a small amount of antigens, and then it becomes possible to produce a large amount of antibodies from a single ostrich by growing up to be adult for about ten months and additional immunization.

Thus, by using the ostrich, it becomes possible to easily produce such antibodies, specifically detecting proteins (or part thereof), that were difficult to produce by conventional methods. In addition, the antibody of the present invention has an advantage in commercial use (as an antibody for diagnosis and treatment), since it can be produced in large quantities and homogeneously without lot-to-lot variation.

Here, "antibody" means the protein that specifically binds to and detects an antigen. The kinds of antibodies are not particularly limited (for example, an antibody may be IgG, IgM, IgA, IgD, IgE or IgY). The antibody of the present invention may be monovalent or multivalent. Also, the antibody may be labeled with a fluorescent substance, a radioactive substance, an enzyme or other proteins (such as avidin). Or, the antibody of the present invention may be not labeled and a secondary antibody, binding to and detecting a primary antibody of the present invention, may be used in order to detect a target molecule.

In this DESCRIPTION, "ostrich" means one of the birds that belong to the Struthioniformes. Among the birds, it is preferable to use the *Struthio camelus* that belongs to the Struthionidae. A female or male ostrich may be used. Here, "using an ostrich" means that the ostrich is used as an animal to which an antigen is administered for the production of an antibody. A substance, which is administered as an antigen, is not particularly limited. Proteins, peptides (including nature peptides, synthetic peptides and recombinant peptides), polysaccharides and other biological substances are available as an antigen. Also, a method for preparing and administering an antigen is not particularly limited, although preferable embodiments are described later.

In the Examples described later, the antibody to human CD166 protein was produced by immunizing (vaccinating) an infant ostrich against a synthetic peptide, which was used as antigen. The synthetic peptide consisted of 20 amino acids, which are located in the fourth Ig loop of the extracellular region and highly reserved among the mammals. Thus produced anti-CD166 ostrich antibody turned out to be able to specifically detect human CD166 protein which is a cancer marker (FIGS. 1 and 3) and thus, it can be used as an antibody for diagnosis of cancer. Moreover, it was found out that the above anti-CD166 ostrich antibody had antitumor effect of suppressing tumor growth (FIG. 4), which means that the above antibody can be also used as an antibody for treatment of cancer. Thus, by using the ostrich, it becomes possible to easily produce an antibody for medical use (that is, an antibody for diagnosis or treatment), which was difficult to produce by conventional methods using the mammals.

Of course, in the production of antibody to human CD166 protein, a used antigen is not limited to the above-mentioned synthetic peptide. The whole human CD166 protein, or part thereof consisting of a specific sequence (preferably about 10-20 residues), can be also used as an antigen. By a similar method, other anti-CD antibodies (antibodies to CD antigens other than CD166) may be produced. Here, CD (Cluster of differentiation) means an antigen of a cell surface (for example, an adhesive molecule), to which a specific number is denominated according to the CD classification. The above-mentioned CD166 is one of CDs. The present invention, i.e., a method for producing an antibody by using the ostrich, can realize easy production of a large amount of homogeneous anti-human CD antibodies with high detecting ability.

As described above, use of an infant ostrich has the advantage that the immunization can be realized by a small amount of antigens. Therefore, it is preferable to produce the antibody of the present invention by firstly immunizing an infant ostrich. Specifically, an infant ostrich, which is firstly immunized, may be preferably at not less than the age of two months and half, and at less than the age of ten months. More preferably, an infant ostrich, which is firstly immunized, may be at not less than the age of three months, and at less than the age of seven months. It is much more preferable to firstly immunize an infant ostrich at not less than the age of three months, and at less than the age of five months.

The following are descriptions of advantages and preferable embodiments of the production of an antibody by using the ostrich;

(1) The ostrich grows up rapidly from its hatch (about 0.8 kg in weight) and will reach 60 kg at the age of six months and 120 kg at the age of ten months (adult). This means that, by starting the immunization from an infant bird, small amount of antigens and several times of additional immunizations are sufficient to obtain a large amount of antibodies.

(2) The following is one example of methods for production of antibodies; a synthetic peptide can be used as an antigen and the antigen dose for immunization is 100 μg per once. The ostrich is first immunized at the age of three months and then, immunized at the same antigen dose every month to grow up to be adult. (In the Example described later, the ostrich was immunized every other week, and three times in total.) In the first immunization, 0.5 mL of solution with 100 μg antigen is mixed with 0.5 mL of complete adjuvant, and the mixture is vaccinated into the breast muscle of the ostrich. From the second immunization, 0.5 mL of solution with 100 μg antigen is mixed with 0.5 mL of incomplete adjuvant, and the mixture is vaccinated into the neck muscle of the ostrich. Blood of the immunized ostrich is collected 2-5 days after the final immunization and antibodies are purified from the antiserum in the blood by using a protein G column.

(3) For measurement of the antibody titer, it is preferable to collect blood from the wing vein of the immunized ostrich until the age of four months and from the jugular vein after that age. (After the age of five months, the ostrich becomes brutal.)

(4) It is preferable to start the immunization after the age of three months, since an infant ostrich is weak to stress before the age of two months.

(5) As a result of immunizing an ostrich by the method described in the above (2), the rise of the antibody titer was already confirmed at the time of the third immunization (at the age of five months). The antibody titer reached the highest value at the time of the fifth immunization (at the age of seven months). It is possible to produce antibodies at this stage by collecting a large amount of blood of the immunized ostrich. However, the highest value of the antibody titer can be maintained by extension of breeding period and additional immunization until the adult (120 kg in weight). Therefore, it is possible to produce much more antibodies at the adult.

(6) The antibody can be continuously collected as long as the immunized ostrich is not dead and thus, it is possible to continuously provide antibodies.

(7) Antibodies of the bird can move to its egg. The egg of the immunized ostrich may include antibodies with high concentration. That is, the egg may be used in order to collect antibodies continuously, easily and in large quantities, which is also described later.

(8) It is preferable to use a protein G in the purification of antibodies IgG obtained by immunizing an ostrich, since a protein A is weak at binding to these antibodies.

The following are descriptions of further advantages and preferable embodiments of the production of an antibody by using the ostrich, and examples of industrial application of the produced antibody. By using the ostrich, the present invention can produce high sensitive antibodies in large quantities homogeneously and in a simple manner, as compared with the production by using the chicken or other animals. For example, two kinds of antibodies, i.e., the antibody to human CD146 and the antibody to human CD166, were produced by using the ostrich and the chicken. Then, antigen-detecting abilities of two kinds of ostrich antibodies were respectively compared with those of two kinds of antibodies produced by using the chicken. The result was that both ostrich antibodies had higher antigen-detecting abilities than the chicken antibodies (FIGS. 8 and 9) and thus, the ostrich antibodies have qualitative advantage.

As described in the above (7), it is possible to produce a large amount of antibodies continuously and easily, by immunizing a female ostrich against an antigen and then purifying antibodies (IgY) from the yolk of the egg produced by that female ostrich. For example, a female ostrich, producing eggs, was immunized every week against Collagen Type I as an antigen. As a result, four weeks after the first immunization, the production of antibodies was confirmed in the yolk of the egg produced by that female ostrich (FIGS. 5 and 6). In a similar way, a female ostrich, producing eggs, was immunized every week against an inactivated vaccine of IBV (Infectious Bronchitis Virus). As a result, six weeks after the first immunization, the production of antibodies was confirmed in the yolk of the egg produced by that female ostrich (FIG. 7).

Moreover, by adopting the method for purification of IgY, 2-4 g of antibodies (IgY) were purified per the yolk of a single egg produced by the female ostrich of six weeks after the first immunization. During the ostrich egg producing period ranging from April to September, a single female ostrich produces about 100 eggs, from which about 400 g of antibodies (IgY)

can be produced at maximum. This means that, for example if producing a diagnosis kit for testing virus infection, a single female ostrich can produce a large amount of antibodies that can be used as diagnosis kits for testing about 4-40 million samples, at the time of six months after the first immunization by adjusting the timing of immunization.

The method for purification of IgY from an ostrich egg yolk may adopt essentially the same method as that for purification of IgY from a chicken egg yolk (for example, see J. Immunol. Methods 46: 63-68, 1981; Agric. Biol. Chem. 54: 2531-2535, 1990; Immunological Investigations 19: 253-258, 1990.). Commercial kit for purification of antibodies (IgY) from a chicken egg yolk may be used for purification of antibodies (IgY) from an ostrich egg yolk, although it is preferable to increase up to about 1.5 times the amount of all the reagents (for example, dextran sulfate/TBS), as compared with purification from a chicken egg yolk, since the ostrich egg yolk includes more lipids.

The antibody of the present invention can be used in various fields and its use is not particularly limited. The antibody of the present invention can be used as antibodies presently used in various fields, in addition to antibodies for medical use as described above. Especially, the antibody of the present invention can be mass-produced by using an ostrich. Therefore, by applying the present invention to the production of antibodies for examination (used as a kit for examining cancer and a kit for examining viral infection, etc.), it becomes possible to easily and promptly prepare a large amount of examination kits from a single ostrich, which are required to examine enormous samples in the examinations of physical condition, infectious disease and food poisoning.

For example, it becomes possible to produce a large amount of antibodies against SARS (Severe Acute Respiratory Syndrome) virus by using an ostrich, since the abovementioned IBV (Infectious Bronchitis Virus) is a coronavirus close to the SARS virus. It is also possible to produce a large amount of antibodies for detection of pathogenic viruses such as Avian Influenza Virus. Moreover, it is possible to produce a large amount of antibodies for examination of prion diseases such as BSE (Bovine Spongiform Encephalopathy) and other diseases. In addition, the antibody of the present invention can be used as an industrial antibody. That is, it can be used as antibodies for removal of pathogenic substances, allergens or other antigens, which can be applied in various industrial products such as an air conditioner filter, a face mask and a water filter.

Thus, the present invention can be used as an industrial antibody for removal of virus by applying to an air conditioner filter, a face mask and other products, in addition to using as antibodies for detection of virus or antibodies for examination of diseases. Of course, it is possible to apply to an antibody for detection and/or removal of pathogenic substances (such as bacteria causing infectious disease or food poisoning), allergens in food (such as buckwheat and ovalbumin) and pathogenic substances within drinking water.

The antibody of the present invention may be produced as a polyclonal antibody or a monoclonal antibody. General production method of such antibody is described in, for example, "Antibodies: A laboratory manual" written by Harlow et al., Cold Spring Harbor Laboratory, New York (1988) and "Monoclonal antibody: Hybridoma and ELIZA" written by Iwasaki et al., Kodansha (1991). The following is a brief explanation of the production method of a polyclonal antibody and a monoclonal antibody.

(1) Production of Polyclonal Antibodies

The polyclonal antibody may be produced by the following method; firstly, a substance is administered to an ostrich as an antigen. The substance may be administered alone or with other substance such as a carrier and a diluent. The substance may be administered to, for example, the breast muscle and the neck muscle of the ostrich, as described above, which enables the production of antibodies in the ostrich. To improve the productivity of antibodies, the substance may be administered with Freund's complete or incomplete adjuvant. The antigen may be administered once only. However, the antigen is usually administered once every 2-6 weeks and administered about 2-10 times in total.

Antibody titer to the antigen in the ostrich serum may be measured by a liquid phase method or a solid phase method. In the liquid phase method, for example, labeled antigen is reacted to the antiserum and then, the activity of labeling agents binding to antibodies is measured. In the solid phase method, for example, the antigen is immobilized to an inner wall of each well in 96 hole plate and then, the diluted serum is added to each well, in order to bind antibodies to the antigen, followed by removal of extra antibodies by washing the solution in each well. Then, antibodies binding to the inner wall of each well are measured.

Polyclonal antibodies of the present invention may be purified by a method for separation and purification of immunoglobulin. Such method includes salting-out method, alcohol precipitation method, isoelectric precipitation method, electrophoresis, adsorption and desorption by an ion exchanger such as DEAE, ultracentrifugal method, gel filtration technique and antigen binding solid phase method, in addition to specific purification method for obtaining antibodies by collecting antibodies with an activated adsorbent such as a protein G and then dissociating the antibodies from the adsorbent.

(2) Production of Monoclonal Antibodies

The monoclonal antibody may be produced by the following method; firstly, among ostriches which have been immunized against an antigen, the ostriches having antibodies are selected. After collecting the spleen or the lymph node of these ostriches 2-5 days after the final immunization, an antibody-producing cell contained in such organ is fused with a myeloma cell, so as to prepare a hybridoma producing an antibody of the present invention.

The fusion technique may be carried out according to any of known methods, for example, Kayler and Milstein method (Nature Vol. 256, Page 495 (1975)). As a fusion promoting agent, polyethylene glycol (PEG) and Sendai virus are exemplified, and preferably PEG may be used. As the myeloma cell, NS-1, P3U1, SP2/0 and AP-1 are exemplified, and preferably P3U1 may be used. In the fusion, preferable ratio of the number of the antibody-producing cells (such as spleen cells) and the number of the myeloma cells is usually about at 1:1-20:1. The cell fusion may be efficiently performed by adding PEG (preferably PEG1000-PEG6000) in the concentration of about 10-80%, and incubating for 1-10 minutes usually at 20-40° C. (preferably at 30-37° C.).

Antibody-producing hybridoma may be screened by various methods. Such methods include the following methods. For example, a supernatant of cultured hybridoma is added to a solid phase (such as a microplate) in which an antigen or its partial peptide is immobilized directly or with a carrier. Next, added is an anti-ostrich immunoglobulin antibody or a protein G, which is labeled with a fluorescent substance or an enzyme etc., in order to detect a monoclonal antibody of the present invention, binding to the solid phase. In another method, the antibody-producing hybridoma is added to a solid phase in which an anti-ostrich immunoglobulin antibody or a protein G is immobilized. Next, added is an antigen labeled with a fluorescent substance or an enzyme etc., in order to detect a monoclonal antibody binding to the solid phase.

Screening of a monoclonal antibody of the present invention and culture for such screening may be performed by adding HAT (hypoxanthine, aminopterin and thymidine) to a medium for culture of animal cells (such as RPMI1640) including 10-20% fetal bovine serum. Antibody titer of a supernatant of cultured hybridoma may be measured by the same method as the above-mentioned method used for measurement of the antibody titer in the antiserum. Monoclonal antibodies of the present invention may be separated and purified by the same method as the above-mentioned method used for separation and purification of polyclonal antibodies.

Thus, the monoclonal antibody of the present invention may be produced by culturing a hybridoma cell in an animal body or in vitro, and then collecting monoclonal antibodies from a body fluid or a culture.

Of course, the method for producing polyclonal and monoclonal antibodies of the present invention are not limited to the above-mentioned methods, and various known methods and techniques may be applied. Newly developed methods and techniques may be also applied.

EXAMPLES

Examples of the present invention are described below in reference to the drawings. The present invention is, however, never limited by these Examples.

Example 1

Produced was the antibody against human CD166 protein which may be used as a marker of various cancers such as lung cancer, melanoma and prostate cancer. In this production, a synthetic peptide was used as the antigen; i.e., twenty amino acids in the fourth Ig loop of the extracellular region, which are highly reserved among the mammals. The sequence of the twenty amino acids is all the same among the human, the mouse and the rabbit. Using the synthetic peptide, the mouse (BALBc), the rabbit (white kind of Japan) and the ostrich (an infant at the age of three months) were immunized every other week (total three times) and then, each blood was collected.

Figure 1:
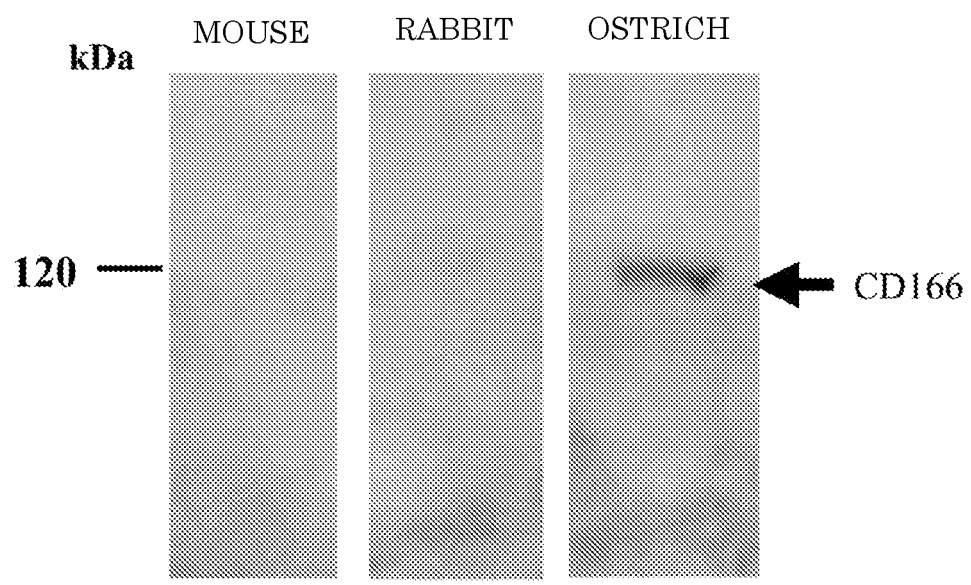
FIG. 1 is a figure showing the result of detecting human CD166 protein by western blot analysis using each antiserum of the mouse, the rabbit and the ostrich, after immunizing these animals against human CD166 peptide.

The first immunization was a mixture of the liquid (0.5 mL) with 100 μg of antigen and 0.5 mL of complete adjuvant, and the mixture was injected for vaccination into the breast muscle of the ostrich and into the dorsal skin of the rabbit respectively. 0.4 mL of this mixture was injected for vaccination into the dorsal skin of the mouse. From the second immunization, a mixture of the liquid (0.5 mL) with 100 μg of antigen and 0.5 mL of incomplete adjuvant was used for vaccination by injecting the mixture into the neck muscle of the ostrich and into the dorsal skin of the rabbit respectively. 0.4 mL of this mixture was injected for vaccination into the dorsal skin of the mouse. Then, western blotting was carried out using antisera obtained from these animals, to the fraction of cell membrane of human lung cancer. The antisera were obtained two weeks after the final immunization. As a result, only the ostrich was able to produce antibodies which can detect human CD166 protein (FIG. 1).

Figure 2:
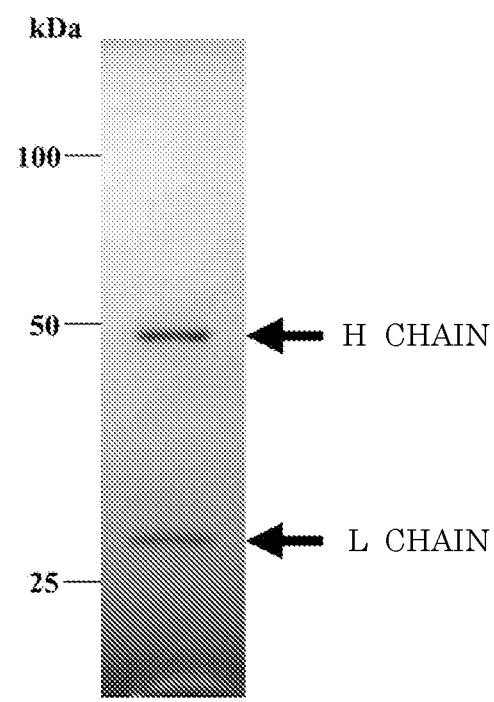
FIG. 2 is a figure showing the result of confirming the existence of purified ostrich IgG by SDS-PAGE.

In the western blotting, labeled secondary antibody was used. The method for production of this secondary antibody is as follows; firstly, immunoglobulin G (IgG) was purified from the blood of non-immunized ostrich by using a protein G, and confirmed by SDS-PAGE (FIG. 2). Then, the rabbit was immunized against this ostrich IgG. Specifically, the rabbit (white kind of Japan) was immunized every other week (total four times) against 200 μg of the ostrich IgG per once. The whole blood was collected from the rabbit two weeks after the final time, to produce anti-ostrich IgG rabbit polyclonal antibody (serum). Purification procedure was carried out according to a normal method using a protein A. Thus purified antibody was labeled with FITC or HRP and used as the secondary antibody.

The antibody was purified from the above-mentioned ostrich antiserum by the following method; firstly, the ostrich antiserum was loaded onto a protein G column. After it was washed with PBS, the antibody was eluted with a mixture (pH 9.0) of a citrate buffer and a glycine buffer, and then neutralized with 2M Tris/HCl. Thus, the antibody was obtained and used in the following experiments as an anti-CD166 ostrich antibody.

Example 2

Figure 3:
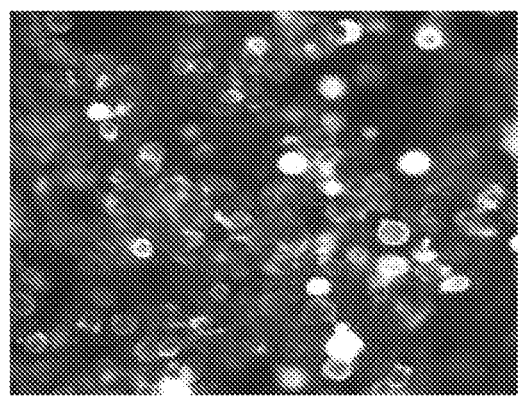
FIG. 3 is a figure showing the result of detecting human CD166 protein in human lung cancer cells (A549 cells), by immunocytochemical technique using the anti-CD166 ostrich antibodies.

Using the anti-CD166 ostrich antibody produced by Example 1 as a primary antibody, immunofluorescence assay was carried out to cultured human lung cancer cells (A549 cells). As a result, the antibody strongly reacted to the cell membranes of the lung cancer cells (FIG. 3). In this experiment, at first, the A549 cells were cultured during a whole day on a coverslip, and then fixed with the Zamboni solution. Next, the anti-CD166 ostrich antibody (1 mg/mL) produced by Example 1 was diluted to 1000 times with PBS, and the antibody was used as a primary antibody in the reaction with the A549 cells for one hour at 37° C. Then, the reaction using a secondary antibody was carried out. FITC labeled anti-ostrich IgG rabbit polyclonal antibody (1 mg/mL) produced by Example 1 was diluted to 1000 times with PBS, and the antibody was used as a secondary antibody in the reaction with the A549 cells for one hour at 37° C. After the reaction, the A549 cells were observed with fluorescence microscope.

Example 3

Figure 4:
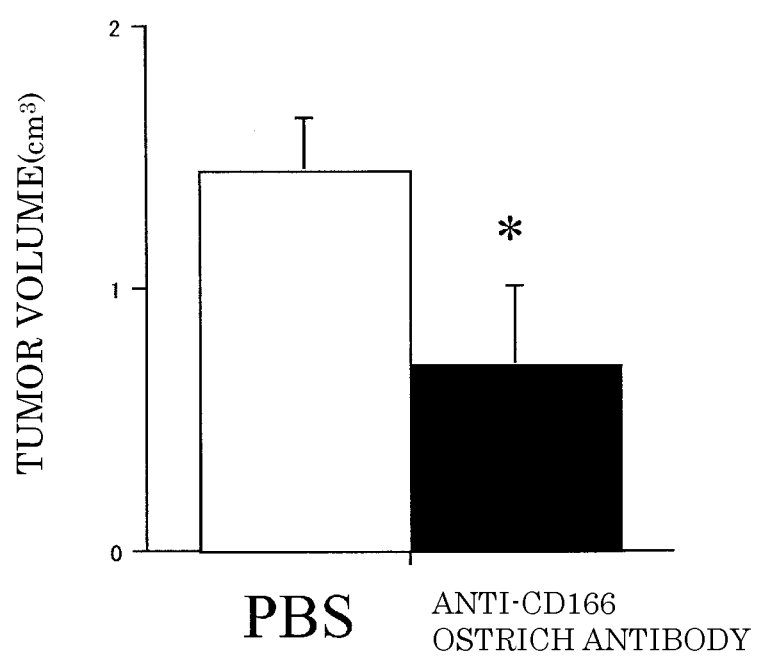
FIG. 4 is a graph showing the result of investigation of in vivo antitumor effect of the anti-CD166 ostrich antibodies administered to a nude mouse into which human lung cancer cells have been implanted. The sign "*" shows a significant difference compared with the case where PBS was administered. *P<0.01 (Student-t)

$10^6$ of cultured human lung cancer cells (A549 cells) were subcutaneously transplanted to each of five nude mice. From five days after the transplant, the anti-CD166 ostrich antibody (120 μg) produced by Example 1 was intraperitoneously administered every week, and tumor volume of each mouse was measured three weeks after the transplant. Only PBS was administered to a control mouse. As a result, it turned out that tumor growth was significantly suppressed in the group to which the anti-CD166 ostrich antibody was administered (FIG. 4).

Example 4

In order to investigate the production of antibodies into an egg yolk, a female ostrich at the age of two years and six months, producing eggs, was immunized every week against rat Collagen Type I. Then, the production of antibodies was examined in the serum at one to three weeks after the first immunization and in the yolk extract at four weeks after the first immunization, by precipitation reaction in agarose gel. The following is a detailed explanation of this experiment.

Antigen dose and method for immunization: Antigen solution (4 mg/0.5 mL) was mixed with 0.5 mL of complete adjuvant, and injected for vaccination into the dorsal skin of the ostrich. As an additional immunization, the antigen solution (4 mg/0.5 mL) was mixed with 0.5 mL of incomplete adjuvant, and injected for vaccination into the dorsal skin of the ostrich.

Purification of serum: Blood was collected from the jugular vein of the ostrich, and left for one hour. After that, the serum was separated by centrifugal separation (15,000 rpm).

Yolk extract: Only yolk (250-350 mL) was collected from the ostrich egg, and stirred. Only 10 mL of this liquid egg yolk was used and the remainder was preserved in a freezer. 10 mL of the liquid egg yolk was mixed with 75 mL of TBS (20 mM Tris-HCl (pH7.5), 0.15 M NaCl, 0.5% $NaN_3$). After 5 mL of 10% dextran sulfate/TBS was added, the mixture was stirred for 30 minutes. Moreover, after 10 mL of 1 M CaCl/TBS was added, the mixture was stirred and left for two hours or more. Supernatants were collected after the centrifugation for 30 minutes by 10,000 rpm. Ammonium sulfate was added to the supernatants so as to become 40% in the final concentration and left for 12 hours or more. Then, precipitation was collected after the centrifugation by 10,000 rpm. This precipitation was resuspended in 10 mL of TBS, and dialyzed with TBS.

Precipitation reaction in agarose gel: Agarose was added to 0.8% NaCl solution so as to become 1% in the final concentration and completely dissolved by heating. The solution was mounted onto a slide glass and cooled so as to form the structure having one hole in the center and six holes in the surroundings. 30 μl of the antigen solution (2 mg/ml) was dropped to the center hole, while 30 μl of PBS, the serum or the yolk extract was dropped to the surrounding holes. After 12 hours, the existence of any precipitation line was observed.

Figure 5:
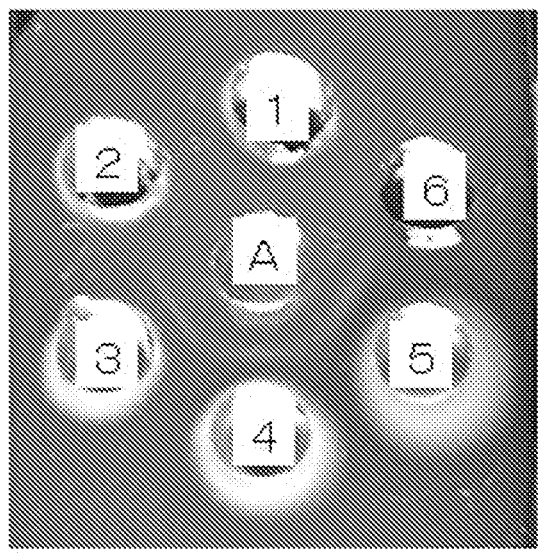
FIG. 5 is a figure showing the result of examining the production of antibodies in the sera of immunized female ostriches (producing eggs) and in the yolks of their eggs by precipitation reaction in agarose gel. In this examination, female ostriches have been immunized against Collagen Type I. In this figure, A: the antigen (Collagen Type I), 1: the ostrich serum before immunization, 2: the ostrich serum one week after immunization, 3: the ostrich serum two weeks after immunization, 4: the ostrich serum three weeks after immunization, 5: the extract from the ostrich egg yolk four weeks after immunization, 6: PBS. The white precipitation line occurred by the antigen-antibody reaction shows the production of antibodies.

FIG. 5 shows the result. The signs and numbers in this figure are as follows;
A: the antigen (Collagen Type I)
1: the ostrich serum before immunization
2: the ostrich serum one week after immunization
3: the ostrich serum two weeks after immunization
4: the ostrich serum three weeks after immunization
5: the extract from the ostrich egg yolk four weeks after immunization
6: PBS.

Figure 6:
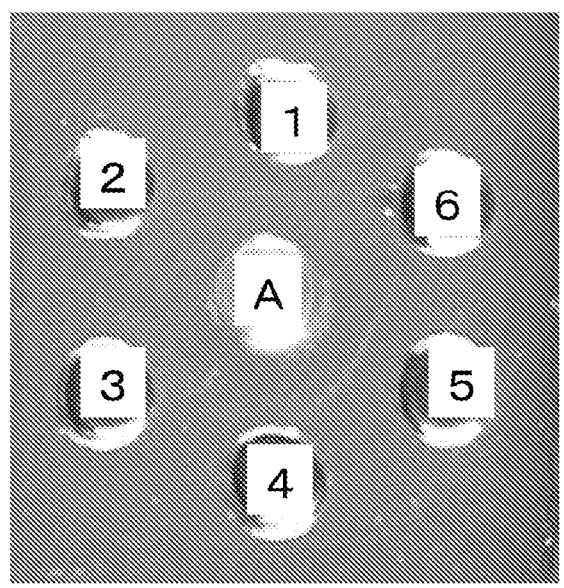
FIG. 6 is a figure showing the result of examining the production of antibodies in the egg yolks of immunized female ostriches by precipitation reaction in agarose gel. In this examination, female ostriches have been immunized against Collagen Type I. In this figure, A: the antigen (Collagen Type I), 1: the extract from the ostrich egg yolk before immunization, 2: the extract from the ostrich egg yolk one week after immunization, 3: the extract from the ostrich egg yolk two weeks after immunization, 4: the extract from the ostrich egg yolk three weeks after immunization, 5: the extract from the ostrich egg yolk four weeks after immunization, 6: PBS. The white precipitation line occurred by the antigen-antibody reaction shows the production of antibodies.

In a similar way, the production of antibodies in the egg yolks of immunized female ostriches was examined by the precipitation reaction in agarose gel. In this examination, female ostriches were immunized every week against rat Collagen Type I. Then, examined was the production of antibodies in the yolk extract made from the ostrich at one to four weeks after the first immunization. FIG. 6 shows the result. The signs and numbers in this figure are as follows;
A: the antigen (Collagen Type I)
1: the extract from the ostrich egg yolk before immunization
2: the extract from the ostrich egg yolk one week after immunization
3: the extract from the ostrich egg yolk two weeks after immunization
4: the extract from the ostrich egg yolk three weeks after immunization
5: the extract from the ostrich egg yolk four weeks after immunization
6: PBS In FIGS. 5 and 6, the white precipitation line occurred by the antigen-antibody reaction shows the production of antibodies (also in FIG. 7). As shown in these figures, antibodies are produced both in the blood of the immunized ostrich at two weeks after immunization and in the ostrich egg yolk at four weeks after immunization. Thus, the production of antibodies was confirmed in the ostrich egg yolk.

Figure 7:
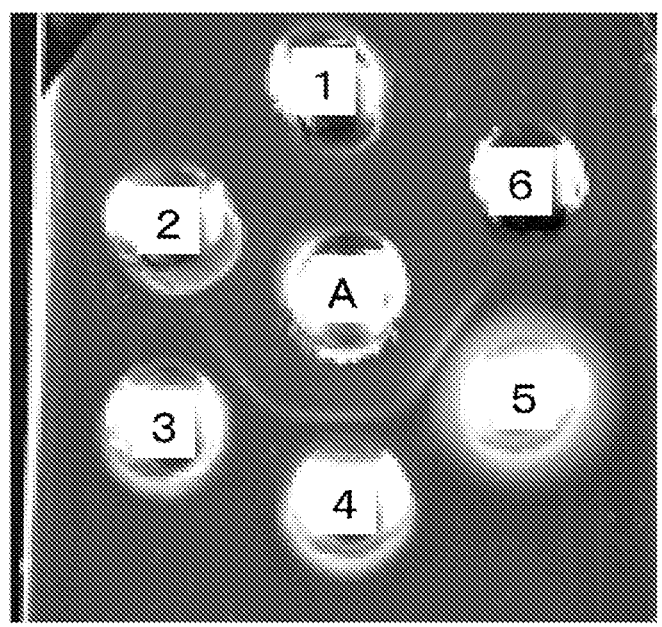
FIG. 7 is a figure showing the result of examining the production of antibodies in the sera of immunized female ostriches (producing eggs) and in the yolks of their eggs by precipitation reaction in agarose gel. In this examination, female ostriches have been immunized against an inactivated vaccine of IBV (Infectious Bronchitis Virus). In this figure, A: the antigen (IBV), 1: PBS, 2: the ostrich serum before immunization, 3: the ostrich serum four weeks after immunization, 4: the ostrich serum six weeks after immunization, 5: the extract from the ostrich egg yolk six weeks after immunization, 6: the extract from the ostrich egg yolk before immunization. The white precipitation line occurred by the antigen-antibody reaction shows the production of antibodies.

The production of antibodies in the sera of female ostriches (producing eggs) and in the yolks of their eggs was further examined by the precipitation reaction in agarose gel. In this examination, female ostriches were immunized every week against an inactivated vaccine of IBV (Infectious Bronchitis Virus). Then, examined was the production of antibodies in the sera and the egg yolks. FIG. 7 shows the result. The signs and numbers in this figure are as follows;

A: the antigen (IBV)
1: PBS
2: the ostrich serum before immunization
3: the ostrich serum four weeks after immunization
4: the ostrich serum six weeks after immunization
5: the extract from the ostrich egg yolk six weeks after immunization
6: the extract from the ostrich egg yolk before immunization As shown in FIG. 7, antibodies are produced in the sera of the immunized ostriches at four and six weeks after the first immunization and in the extract from the ostrich egg yolk at six weeks after the first immunization. Thus, the production of antibodies was confirmed in the ostrich egg yolk.

Example 5

In order to compare antigen-detecting abilities between the ostrich antibody and the chicken antibody, anti-CD146 antibodies were produced respectively by using the ostrich and the chicken.

In this experiment, female chickens and female ostriches were immunized against human CD146 proteins every other week. Then, these sera were collected six weeks after immunization, in order to purify antibodies. The antibodies were respectively labeled with HRP equivalent (0.1 mg). 10 ng of the CD146 protein was subjected to SDS-PAGE and transferred to a PVDF membrane. Then, the PVDF membrane was subjected to reaction with each of the above-mentioned antibodies. After the reaction, the PVDF membrane was washed and subjected to light emitting reaction with ECL, followed by exposure to a roentgen film.

Figure 8:
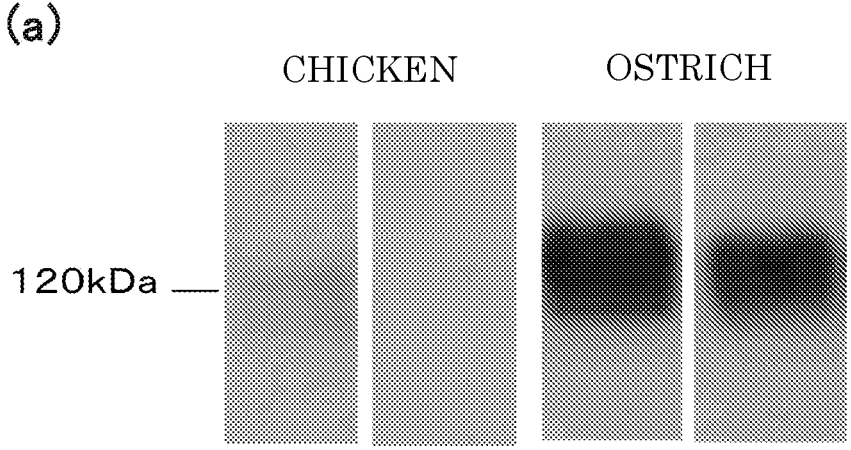
FIG. 8 is a figure showing the result of investigation in which anti-CD146 antibodies were produced respectively by using the ostrich and the chicken, and then antigen-detecting abilities of both antibodies were compared. (a) result of immunoblot analysis using each antibody, (b) graph showing relative intensity of both antibodies. The sign "*" shows a significant difference compared with the antibody produced by using the chicken. *P<0.01 (Student-t)
Figure 8:
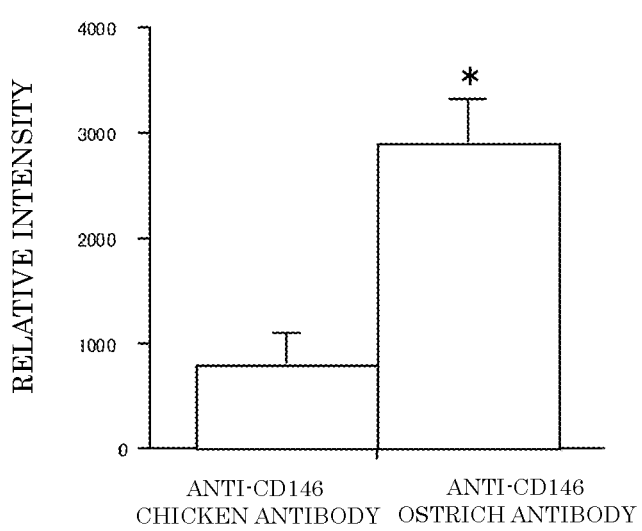

FIG. 8 shows the result. (a) in this figure shows the result of immunoblot using respective antibodies produced from two chickens and two ostriches. As shown, the ostrich antibodies had higher antigen-detecting ability than the chicken antibodies. (b) in this figure is a graph showing relative intensity of both antibodies. The relative intensity is an average respectively of three chickens and three ostriches. The relative intensity was calculated as follows; i.e., the density of each band on the roentgen film was measured by a densitometry, and the relative intensity was calculated in which the intensity of area with no bands was set as "1". As shown, the ostrich antibodies had higher relative intensity than the chicken antibodies.

In a similar way, anti-CD166 antibodies were produced respectively by using the ostrich and the chicken, in order to compare antigen-detecting abilities of both antibodies. In this experiment, female chickens and female ostriches were immunized against human CD166 proteins every other week. Then, these sera were collected six weeks after immunization, in order to purify antibodies. The antibodies were respectively labeled with HRP equivalent (0.1 mg). 20 ng of the CD166 protein was subjected to SDS-PAGE and transferred to a PVDF membrane. Then, the PVDF membrane was subjected to reaction with each of the above-mentioned antibodies. After the reaction, the PVDF membrane was washed and subjected to light emitting reaction with ECL, followed by exposure to a roentgen film.

Figure 9:
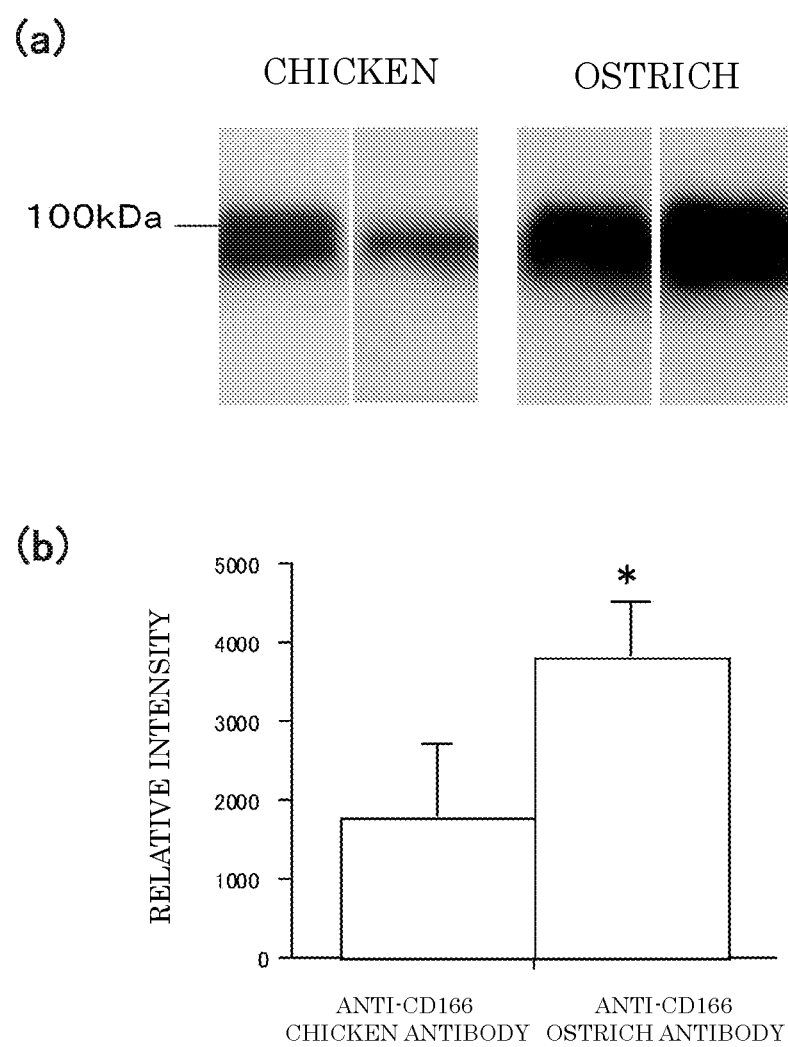
FIG. 9 is a figure showing the result of investigation in which anti-CD166 antibodies were produced respectively by using the ostrich and the chicken, and then antigen-detecting abilities of both antibodies were compared. (a) result of immunoblot analysis using each antibody, (b) graph showing relative intensity of both antibodies. The sign "*" shows a significant difference compared with the antibody produced by using the chicken. *P<0.01 (Student-t)

FIG. 9 shows the result. (a) in this figure shows the result of immunoblot using respective antibodies produced from two chickens and two ostriches. As shown, the ostrich antibodies had higher antigen-detecting ability than the chicken antibodies. (b) in this figure is a graph showing relative intensity of both antibodies. The relative intensity is an average respectively of three chickens and three ostriches. The relative intensity was calculated as follows; i.e., the density of each band on the roentgen film was measured by a densitometry, and the relative intensity was calculated in which the intensity of area with no bands was set as "1". As shown, the ostrich antibodies had higher relative intensity than the chicken antibodies. Thus, the ostrich antibodies had higher detection ability than the chicken antibodies, and it was confirmed by this Example that the ostrich antibody has qualitative advantage.

Industrial Applicability

As described, the present invention relates to an antibody produced using an ostrich and a method for production thereof. The present invention is useful not only for mass production of antibodies for medical use, which are antibodies for treatment or diagnosis, but also for other various fields where antibodies may be used.

What is claimed is:

1. A method of producing an ostrich antibody having binding specificity for a viral protein or a peptide thereof, comprising the steps of:
  a. administering to an ostrich of 2.5 to 10 months of age a viral protein or a peptide fragment thereof as an antigen,
  b. permitting in vivo production of an ostrich antibody against the protein or the peptide fragment thereof, where the ostrich antibody specifically binds to the protein or the peptide fragment thereof,
  c. isolating the ostrich antibody from an ostrich fluid, and
  d. producing a polyclonal antibody having binding specificity for a viral protein or a peptide thereof.

2. The method of producing an ostrich antibody of claim 1, wherein the ostrich is female ostrich and the ostrich fluid is a yolk of an egg from the female ostrich.

* * * * *